(12) United States Patent
Lindström et al.

(10) Patent No.: US 8,000,001 B2
(45) Date of Patent: Aug. 16, 2011

(54) METHOD OF FORMING POLYMERIC MICROARRAY SUPPORT

(75) Inventors: Tomas Lindström, Uppsala (SE); Ove Öhman, Uppsala (SE)

(73) Assignee: Amic AB (SE)

( * ) Notice: Subject to any disclaimer, the term of this patent is extended or adjusted under 35 U.S.C. 154(b) by 1020 days.

(21) Appl. No.: 10/556,961

(22) PCT Filed: May 18, 2004

(86) PCT No.: PCT/SE2004/000761
§ 371 (c)(1),
(2), (4) Date: Nov. 15, 2005

(87) PCT Pub. No.: WO2004/104585
PCT Pub. Date: Dec. 2, 2004

(65) Prior Publication Data
US 2007/0065935 A1      Mar. 22, 2007

(30) Foreign Application Priority Data

May 20, 2003    (SE) ........................................ 0301470

(51) Int. Cl.
*H04B 10/12* (2006.01)
*G02B 5/18* (2006.01)
*G01N 21/00* (2006.01)
*C23F 1/00* (2006.01)
*B29D 11/00* (2006.01)

(52) U.S. Cl. .................... 359/337.21; 359/566; 359/568; 359/569; 359/570; 359/571; 359/572; 359/573; 359/575; 356/337; 422/82.11; 216/2; 216/24

(58) Field of Classification Search ................ 422/99; 435/287.2, 283.1, 288.7, 808; 356/319, 337; 359/337.21, 563, 566–576; 216/2, 24
See application file for complete search history.

(56) References Cited

U.S. PATENT DOCUMENTS

| | | | | |
|---|---|---|---|---|
| 5,143,854 | A * | 9/1992 | Pirrung et al. | 436/518 |
| 5,633,209 | A * | 5/1997 | Leedy | 216/2 |
| 6,143,576 | A | 11/2000 | Buechler | |
| 6,156,270 | A | 12/2000 | Buechler | |
| 6,767,510 | B1 | 7/2004 | Buechler | |
| 6,797,463 | B2 | 9/2004 | Abbott et al. | |
| 2002/0177144 | A1 * | 11/2002 | Remacle et al. | 435/6 |
| 2002/0187249 | A1 * | 12/2002 | Pluster et al. | 427/2.1 |
| 2003/0003457 | A1 * | 1/2003 | Golovlev | 435/6 |
| 2003/0013130 | A1 * | 1/2003 | Charych et al. | 435/7.1 |

(Continued)

FOREIGN PATENT DOCUMENTS

DE    4435752 A1    4/1995

(Continued)

OTHER PUBLICATIONS

Machine Translated Version of JP 07-104112.*
International Search Report issued Aug. 17, 2004, for international application No. PCT/SE2004/000761, filed May 18, 2004, 2 pages.

*Primary Examiner* — Jill Warden
*Assistant Examiner* — Dean Kwak
(74) *Attorney, Agent, or Firm* — Hiscock & Barclay, LLP

(57) ABSTRACT

The invention comprises a polymeric microarray support (1) for an optical assay arrangement (2) comprising optical means (3, 4, 6) for detection of light emitted from the support. The microarray support is provided with microfeatures comprising a surface enlarging pattern (5), i.e. grooves having a selected depth (8). The depth is selected such that the sum of the depth and of the variations in the thickness (7) of the support substantially corresponds to the depth of focus of the optical means.

16 Claims, 2 Drawing Sheets

| U.S. PATENT DOCUMENTS | | | |
|---|---|---|---|
| 2003/0035758 A1 | 2/2003 | Buechler et al. | |
| 2004/0077103 A1 | 4/2004 | Buechler | |
| 2004/0126767 A1 | 7/2004 | Anderberg et al. | |
| 2004/0151626 A1* | 8/2004 | Cunningham et al. | 422/58 |
| 2004/0196455 A1 | 10/2004 | Ermantraut et al. | |
| 2005/0136552 A1 | 6/2005 | Buechler | |
| 2007/0154938 A1 | 7/2007 | Oshida et al. | |

| FOREIGN PATENT DOCUMENTS | | |
|---|---|---|
| EP | 0714742 A2 | 6/1996 |
| JP | 07104112 A | 4/1995 |
| JP | 2001-108684 | 4/2001 |
| JP | 2003-035710 | 2/2003 |
| WO | WO 02/077620 A1 | 10/2002 |

* cited by examiner

US 8,000,001 B2

METHOD OF FORMING POLYMERIC MICROARRAY SUPPORT

CROSS REFERENCE TO RELATED APPLICATIONS

This application is a U.S. national stage application of International application number PCT/SE2004/000761, filed May 18, 2004, which claims priority to Swedish Application Serial No. SE 0301470-1, filed May 20, 2003, both of which are hereby incorporated by reference in their entirety.

TECHNICAL FIELD OF THE INVENTION

The present invention relates to an improved polymeric microarray support for an optical assay arrangement, the microarray support provided with microfeatures comprising a surface enlarging pattern. The invention also relates to an optical assay arrangement comprising an improved polymeric microarray support provided with microfeatures comprising a surface enlarging pattern, and to a method of forming microfeatures comprising a surface enlarging pattern in a polymeric microarray support for an optical assay arrangement.

BACKGROUND OF THE INVENTION

Various fields of research, such as functional genomics, basic life science research, drug discovery and clinical diagnostics, require studying of the molecular mechanisms of a sample, e.g. monitoring of different aspects of oligonucleotides, cDNA or protein interaction. In order to study molecular mechanisms, a microarray-based assay can be used, e.g. an optical assay, such as a fluorescent or a phosphorescent binding assay.

An assay may be performed by a microarray of spots of probe molecules attached to distinct locations on a slide forming a support, the spots of probe molecules providing binding sites for the target molecules of the sample to be analyzed. The diameter of the spots on a microarray support is typically between 50 micrometer and 300 micrometer and normally 100-150 micrometers, and the thickness of the spots are normally only a few micrometer and usually less than 10 micrometer. When a sample, containing e.g. fluorescent-labeled targets, is brought in contact with the spots on the microarray support, the target molecules in the sample is allowed to hybridize with the probe molecules of the spots. In a fluorescent assay, the microarray support is illuminated by an exciting light source and the position and the intensity of the emitted fluorescent light is detected. The color of the used fluorophore serves as a marker indicating that a reaction has occurred between target molecules of the sample and probe molecules of the spots. The optical means for illuminating the support and detecting the light emitted from the support may include a microarray scanner or a microarray imager.

A scanner comprises a narrowband exciting light source, e.g. a laser, and e.g. a PMT (photomultiplier tube) for detecting emitted light. An imager comprises a wideband exciting light source, e.g. a xenon lamp, wavelength filters to provide monochromatic light, and a detector for the emitted light, e.g. a CCD (Charged-Coupled Device).

In microarray technology, there are several benefits by employing polymeric slides for manufacturing of a microarray support instead of glass slides. One of the benefits is that polymeric slides can have a higher density of surface silanol groups than glass slides, which enhances the number of reactive groups participating in the binding process of the probe to the slide, resulting in a higher surface coverage of binding sites. Additionally, polymers exhibit a wider spectrum of properties and are easier to modify, thereby achieving a higher binding capacity. Also, the non-specific binding on polymer slides is normally lower than on glass slides. Furthermore, a higher degree of immobilization is possible on polymer slides, even without UV-crosslinking or blocking, requiring no prehybridization.

However, a drawback with the use of polymer slides is that a higher background signal occurs from autofluorescence in comparison with glass slides.

Prior art in the field of microarray supports is disclosed in WO 01/94032, describing enlargement of the surface of a support by providing pyramidical or conical indentations therein, achieving an increased surface available for the probe. Consequently, an increased number of binding sites may be provided, thereby increasing the signal-to-noise ratio. By surface enlarging patterns, an increase of the available surface area by a factor 2 or 3 is easily obtained, in comparison with planar supports.

US 2002/0028451 describes a detection apparatus comprising a polymeric support substrate provided with microstructured grooves, onto which a liquid crystal material is applied. The size of the grooves is selected to cause the liquid crystal material to adopt a uniform orientation, such that the adherence of particles will be optically detectable by causing a disruption of the uniform orientation.

Further prior art relating to polymeric support provided with high-precision microfeatures is disclosed e.g. in EP 0714742.

However, since there is a need for further improvement of microarray-based optical assays, an object of this invention is to provide an improved polymeric microarray support, achieving a further improved performance of optical assays compared to prior art, e.g. regarding the signal-to-noise ratio.

DESCRIPTION OF THE INVENTION

The above object is achieved by the polymeric microarray support for an optical assay arrangement, as well as by the optical assay arrangement comprising the polymeric microarray support and by the method of forming microfeatures on a polymeric microarray support for an optical assay arrangement, according to the attached claims, which are hereby incorporated in their entirety.

The polymeric microarray support for an optical assay arrangement comprises optical means having a depth of focus for detecting light emitted from the support. The thickness of said support varies over the surface area by a thickness variation value, and the support is provided with selected microfeatures comprising a surface enlarging pattern. The surface enlarging pattern comprises grooves arranged to have a selected depth adapted to said depth of focus of the optical means and to said thickness variation value of the support. By adapting the depth of the grooves such that the sum of said depth and of said thickness variation value substantially corresponds to said depth of focus of the optical means, an improved performance of the optical assay can be achieved, e.g. an increased signal-to-noise ratio. The increase of the signal-to-noise ratio is accomplished both by the increase of the signal due to the enlargement of the support surface area caused by the grooves, resulting in more binding sites, and by the reduced noise/background signal due to the reduced volume of material within the depth of focus.

The grooves may have a selected tilt angle ($\alpha$) relative the support surface adapted to the refractive index of the support material, such that the selected tilt angle ($\alpha$) provides a desired reflectivity of the support surface, both in terms of intensity and of angular properties.

The grooves may have straight or rounded edges, and may be provided in more than one direction on the support surface.

The distance between the individual grooves may be constant or vary over the surface area of the support.

The microfeatures of the support may further comprise an additional layer selected to provide a desired transparency or reflectivity of the support. The additional layer may be of a metallic, a semiconducting or a dielectric material, and may be located on top of the substrate or in the bottom of the substrate.

The microfeatures of the support may further comprise a dielectric mirror, located on top of the substrate or in the bottom of the substrate.

The microfeatures of the support may further comprise a diffractive grating superimposed on at least part of the surface enlarging pattern of the support.

The microfeatures of the support may further comprise light absorbing pigments.

The support may comprise grooves forming pillars, e.g. cylindrically shaped, which may be provided with an additional layer having a larger refractive index than the support material to achieve an optical waveguide.

Particles, e.g. solid or porous, may be provided between the pillars, which further increases the signal-to-noise ratio.

In the method of forming microfeatures comprising grooves in a polymeric microarray support of an optical assay arrangement comprising optical means having a depth of focus for detecting light emitted from said support, the thickness of said support varies over the surface area of the support by a thickness variation value. The depth of said grooves is adapted to said depth of focus and to said thickness variation value by the depth being selected such that the sum of said depth and of said thickness variation value substantially corresponds to said depth of focus, thereby causing an improved performance.

The tilt angle (α) of the grooves, in relation to the support surface, may be adapted to the refracting index of the support material to provide a desired reflectivity of the support surface.

An additional advantage with these surface enlarging grooves is the ability to maintain a capillary flow of fluids.

Other features and further advantages of the invention will be apparent from the following description and the non-limiting example, as well as from the attached claims.

BRIEF DESCRIPTION OF THE DRAWINGS

The present invention will now be described in more detail and with reference to the example and to the drawings, of which.

DESCRIPTION OF PREFERRED EMBODIMENTS

Figure 1:
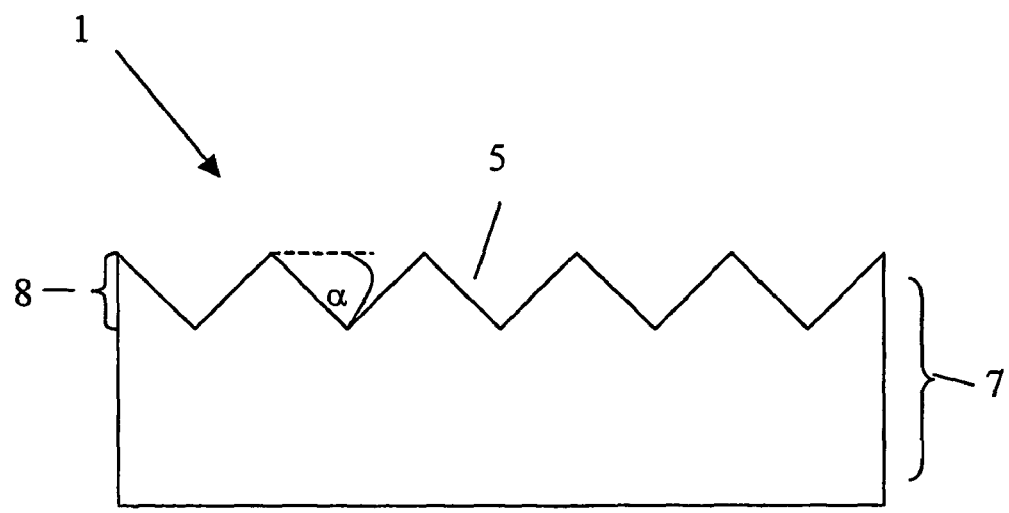
FIG. 1 illustrates a slide forming a microarray support comprising V-shaped grooves with a selected depth and tilt angle relative the support surface.

The terms and expressions used in the description and in the claims are meant to have the meaning normally used by a person skilled in the art.

According to this invention, an improved performance of polymeric microarray supports in optical assays is achieved by incorporating selected microfeatures in the polymeric microarray support, the microfeatures comprising grooves arranged to have a selected depth. The concept of the invention is to improve the performance, e.g. to increase the signal-to-noise ratio, of a microarray support in an optical assay arrangement comprising optical means, by controlling the changes in amplitude (i.e. intensity) and/or in frequency (wavelength) of absorbed, reflected or transmitted light. This is accomplished by providing the microarray support with microfeatures comprising grooves having a depth adapted to the depth of focus of the optical means of the assay arrangement, as well as to the variation of the thickness of the support, such that the sum of the selected depth of the grooves and of the thickness variations of the support substantially corresponds to the depth of focus of the optical means. Preferably, the sum of the selected depth of the grooves and of the thickness variations of the support will be equal to the depth of focus of the optical means. However, the depth of focus may actually be slightly larger or smaller than said sum, depending on the quality of the support slide.

The present invention may be applied e.g. in fluorescent or phosphorescent binding assays, and the selected microfeatures of the polymeric microarray support have the ability to influence the performance of the assay in several ways. The microarray support comprises a substrate provided with a chemically modified surface coating, and the substrate is manufactured from a polymeric slide. The thickness of the support varies over the surface area of the support, and the variation of the thickness is typically less than 15-20 micrometers, depending on the quality of the slide, resulting from the manufacturing method. The microfeatures according to the invention increase the exciting capacity, compared to planar supports, due to an increase of the number of photons in the surface coating where the fluorescent or phosphorescent labels are located. When the labels are fluorescent, the emitting capacity of the support is increased due to an increase of the number of photons emitted from the fluorescent dye reaching the optical detection system, and a reduction of the noise is achieved by avoiding unwanted background fluorescence by reducing the number of photons reaching in and/or out of the substrate of the support.

Thus, the present invention serves to increase the signal-to-noise ratio of optical assays by utilizing selected microfeatures comprising a surface enlarging pattern provided in the polymeric microarray support, the microfeatures selected and adapted to achieve a desired effect of the optical properties of the assay arrangement, of which the optical properties may be described in terms of geometrical optics and/or physical optics. Geometrical optics treats light propagation as a ray phenomenon, while physical optics, on the other hand, utilizes the wave nature of the electromagnetic waves. In geometrical optics the light paths are along rays, whereas, in physical optics, the phenomena of diffraction and interference are present. In geometrical optics, the wavelength of the light is substantially smaller than the size of surface microfeatures, while in physical optics the wavelength of the light corresponds to the size of the surface microfeatures.

In the present invention, the optical means preferably comprises a microarray scanner, which may include confocal optics only collecting emitted light in the depth of focus of the objective lens, e.g. by blocking unwanted light by a pinhole and thereby reducing the detected noise.

Figure 2:
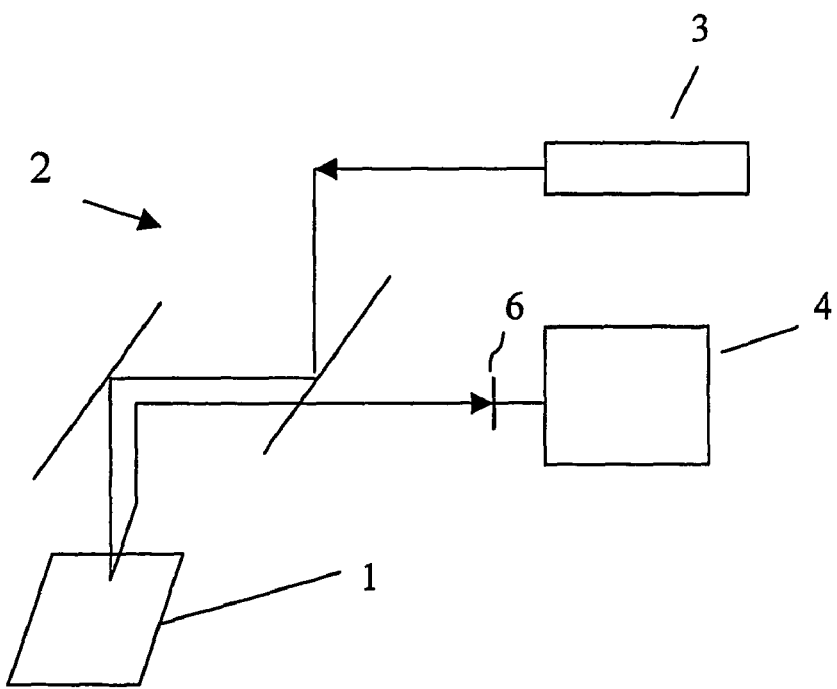
FIG. 2 illustrates a scanning optical assay arrangement comprising a microarray support.

FIG. 2 intends to illustrate one embodiment of a scanning fluorescent assay arrangement 2, comprising a microarray support 1 and optical means 3, 4, 6. The optical means comprises a laser 3 for directing exciting light onto the microarray support, a PMT (Photo Multiplying Tube) 4 for detecting light emitted from the binding sites of the microarray support, and a pinhole 6 for reducing noise.

Figure 3:
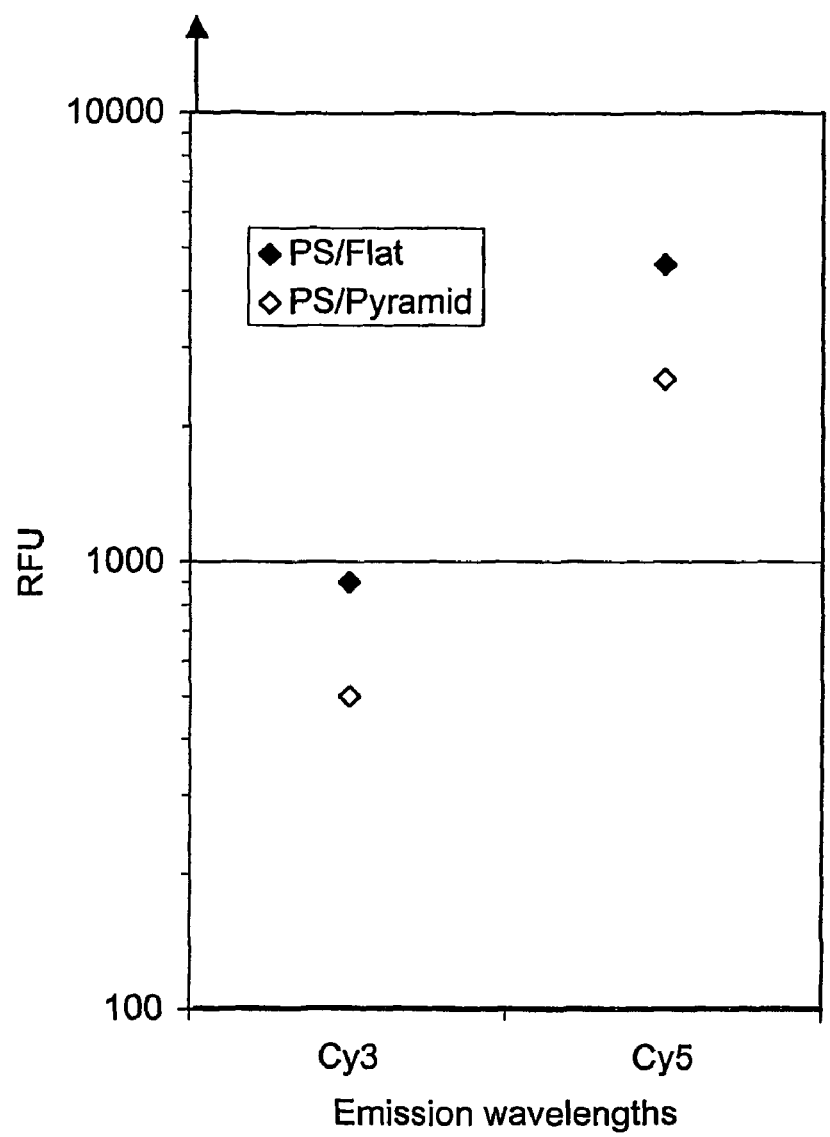
FIG. 3 illustrates a comparison between background fluorescence from flat slides and slides provided with grooves shaped as pyramids.

FIG. 3 illustrates graphically a comparison between the noise contributing background fluorescence as measured in a scanner (cf. FIG. 2) from flat slides and from slides provided with pyramidically shaped grooves. The comparison is performed at two different excitation wavelengths, 543 nm (Cy3) and 633 nm (Cy5) and with polystyrene (PS) as support materials, and the illustrated emission is an average value on the slide. Cy3 is excited at 543 nm and the emission is measured at 570 nm, and Cy5 is excited at 633 nm and the emission is measured at 670 nm. A flat slide is denoted Flat, and a surface covered by pyramids is denoted Pyramid, and a significant reduction of the background fluorescence is achieved with pyramids as compared to flat slides.

The microfeatures of the invented microarray support comprise grooves having a selected depth in relation to the depth of focus of the optical means and to the variation in the thickness of the support. The grooves may have straight or rounded edges, and may e.g. be V-shaped, sinusoidal-, triangular-, trapezoidal- or binary-shaped, or shaped as pillars. The grooves may also be structures in more than one direction on the support. For example, pyramidical grooves can be formed by two adjacent, V-shaped grooves, structured with a 90° angle between the direction of said grooves.

The distance between the individual grooves may be constant or varied over the surface area of the support. The size of the grooves are substantially larger than the wavelength of the exciting light, and a groove may typically have a depth between 5 and 10 micrometer, or even up to 20 micrometer, and may have a tilt angle of e.g. 55°, depending on the optical means and of the desired geometrical optical properties of the support.

FIG. 1 illustrates a side view of one embodiment of the invented microarray support 1 with a thickness 7, that varies over the surface area of support with a thickness variation value (not indicated in the figure) that is equal to the difference between the largest thickness and the smallest thickness of the support, and depends of the quality of the slide. The microarray support is provided with microfeatures comprising a surface enlarging pattern 5, the pattern comprising V-grooves, having a selected depth 8, and tilt angle, α, relative the surface of the support. The support may have an area of e.g. 25 mm×75 mm, and the limited flatness of the slide causes certain variations in the thickness 7 over the area of the support, said variations typically being less than 15-20 micrometers, depending on the manufacturing method. The microarray support may be manufactured by various methods, and preferably by polymer replication formed from a master structure e.g. by injection molding, casting or embossing. The master structure of the groove is typically made in silicon or glass, e.g. by wet or dry chemical etching, by photoresist lithography or by mechanical ruling (e.g. grinding or turning).

According to a first embodiment of the invention, the microfeatures of the support comprise a surface enlarging pattern, e.g. V-grooves, the depth of the grooves being adapted to the depth of focus of the optical means of the assay arrangement, such that the sum of the selected depth of the grooves and of the variation in the thickness of the support substantially corresponds to the depth of focus.

In an exemplary embodiment, the grooves are pyramidically-shaped, the grooves master structure being anisotropically etched in (100) silicon, resulting in a tilt angle of 55°. If the depth of focus of the optical means is 20-30 micrometers and the quality of the support slide limits the variations in the support thickness to 10-15 micrometer, the depth of the grooves, may be selected to e.g. 5-10 micrometer. Thereby, the sum of the depth of the grooves and of the thickness variation over the area of the support slide will be 15-25 micrometer. Consequently, the sum will be well within said depth of focus and also substantially corresponding to the depth of focus. The depth of the grooves may alternatively be selected to be e.g. 10-15 micrometers, resulting in that the sum of the depth of the grooves and of the thickness variation value is 20-30 micrometers, i.e. also substantially corresponding to said depth of focus.

As a result, the signal is increased by the enlargement of the support surface area caused by the grooves, resulting in more binding sites and, consequently, in a higher fluorescent signal. At the same time, the noise/background signal is lowered due to the fact that the volume of autofluorescent material is reduced within the depth of focus.

The grooved structure also results in an increased hydrophobic behavior, since the wetting angle is higher for a structured polymer as compared to a planar polymer, facilitating the printing of high-density microarrays of spots on the support.

Depending on the dimensions of the grooves, they may also be capable of maintaining a capillary flow of fluids.

The tilt angle of the grooves in a support will influence the entrance angle of light incident on the support and change the surface reflection of the support, due to Brewster behavior. The surface reflection can, therefore, be controlled by selecting an appropriate tilt angle of the groove, considering the refractive index of the support material. For example, approximately 4% of circularly polarized light incident on a flat polymer surface is reflected if the polymer has a refractive index of 1.5, and approximately 17% is reflected if the entrance angle of the incident light is 70 degrees, i.e. the reflectivity is increased by a factor 4. The increased surface reflectivity will, in combination with the grooves, also facilitate the incident light to be reflected at least two times on the surface, and, consequently, to excite fluorophores on two distinct locations.

By selecting a proper tilt angle of the grooves, considering the optical constants of both the substrate and of the surface coating material, the direction of the light specularly reflected from the surface can be changed to ensure that the optical path of the emitted light does not follow the optical path of the excitation light. This is advantageous since the excitation energy is substantially larger than the emission energy and the detectors of the microarray scanner, therefore, may be saturated in case the optical paths coincide.

According to a second embodiment of the invention, the performance of the support is further increased by providing a reflecting layer made of a metallic, semiconducting, or a dielectric material. For visible light, a layer of silver, platinum, palladium or gold is beneficial. The thickness of the layer is preferably adapted to the desired transparency of the support, and the layer may be located on the top surface of the support substrate or in the bottom of the support. For example, a 20 nm thick gold film transmits approximately 50% of the red light. One advantage with an additional, metallic layer is that surface chemistry is easier to adopt on a metallic layer than on a polymeric surface. A further advantage is the possibility to use semi-transmitting properties of the layer, i.e. by using the specific wavelength regions of absorption found in metals, semiconductors and dielectrics to make the layer transmit certain wavelengths and reflect other wavelengths.

According to a third embodiment of the invention, the support comprises grooves forming micro-pillars, i.e. cylindrical pillars. According to one exemplary embodiment, the pillars are provided with an additional layer having a larger index of refraction than the support material, thereby achieving an optical waveguide. According to a further exemplary embodiment, particles of suitable size, i.e. typically in the range between 0.1 and 50 micrometers, are located between the micropillars, which improves the signal-to-noise ratio.

According to a fourth embodiment of the invention, the support is provided with a dielectric mirror, comprising an interference layer structure consisting of several layers. The layers may be one quarter of a wavelength thick, comprising alternating oxides, e.g. silicondioxide or titaniumdioxide, with comparatively low and high refractive index, respectively. The dielectric mirror may be located on the top surface of the support substrate or in the bottom of the support. By the interference layer structure, the reflectance in certain wavelengths intervals can be controlled, accomplishing wavelength filtering. By an increased surface reflectance, the noise due to background fluorescence is reduced, since less light is transmitted into the substrate of the support and exciting autofluorescence therein.

According to a fifth embodiment of the invention, the support is provided with a diffractive grating superimposed onto the grooves. The height of the diffractive grating grooves and the distance between the individual grooves of the grating structure is of the same size as the wavelength of the probing light, i.e. in the range of several hundreds nanometers. By the diffractive grating, a further increased surface area enlargement is achieved, as well as a possibility to reflect/transmit selected wavelengths into certain directions. The diffractive grating may also comprise an anti-reflective structure adapted to reduce the surface reflectance of the incident, exciting light, or a reflective-enhancing structure adapted to increase the surface reflectance. The diffractive grating can be produced e.g. by e-beam lithography, and the grating groove structure may e.g. be sinusoidal, triangular, trapezoidal or binary. The grooves of the grating may have straight or rounded edges, and the distance between the individual grooves of the grating may be constant or varied over the grating.

According to a sixth embodiment of the invention, the substrate absorption of the support is adapted to the exciting and/or emitting wavelengths of the exciting light source in order to make the material "optically dead". One way of achieving this is to color the polymer with small light absorbing pigments such that the substrate is absolutely black, i.e. highly absorbing, for the wavelength of interest. Another way to achieve this is by a solvent dye. Also, by mixing particles, e.g. made of quarts, in the polymeric support material, the fluorescent behavior of the support can be reduced.

According to a seventh embodiment of the invention, the support is formed to either transmit or absorb to the wavelength of exciting light and to absorb the wavelength of the used fluorophores. Thereby, the autofluorescence will be prevented to be emitted from the support and to add to the noise.

The invention is not restricted to the described embodiments in the figures, but may be varied freely within the scope of the claims.

The invention claimed is:

1. A method of forming a polymeric microarray support for an optical assay arrangement, said optical assay arrangement comprising an optical detection instrument having a depth of focus for detecting light emitted from said support, wherein said polymeric microarray support comprises a polymeric support surface, wherein the thickness of said polymeric support surface varies over the area of said support surface by a thickness variation value, the forming method comprising the steps of:

determining the depth of focus of said optical detection instrument;

determining the thickness of said support and said thickness variation value;

forming said support with microfeatures comprising grooves arranged to have a depth;

selecting a depth for said grooves in said support surface based on the determined depth of focus of said optical detection instrument and thickness of said support wherein the sum of the depth for said grooves and said thickness variation value of said polymeric support surface substantially corresponds to said depth of focus of said optical detection instrument in order to reduce noise; and attaching probe molecules to said polymeric support surface to form binding sites formed by probe molecules attached to said polymeric surface wherein for said selecting step, the thickness of the support is measured prior to the selection of the depth of said grooves.

2. The method according to claim 1, including the additional step of angling said grooves at a tilt angle ($\alpha$) and wherein said polymeric microarray support comprises a polymeric support material; and angling said tilt angle ($\alpha$) of the grooves relative to said support surface and to the refracting index of said polymeric support material to provide a desired reflectivity of said polymeric support surface.

3. The method according to claim 1, including the step of rounding at least some of said grooves.

4. The method according to claim 1, including the step of forming at least some of said grooves with straight edges.

5. The method according to claim 4, wherein said grooves form pillars.

6. The method according to claim 5, including the step of providing said pillars with an additional layer, wherein the refractive index of said additional layer is selected to be larger than the refractive index of said support to achieve an optical waveguide.

7. The method according to claim 5, wherein said support comprises particles located between said pillars.

8. The method according to claim 1, including the step of forming said grooves in more than one direction on said support.

9. The method according to claim 1, including the step of forming said grooves such that the distance between individual grooves on said support is constant.

10. The method according to claim 1, including the step of forming said grooves such that the distance between individual grooves varies over the surface area of said support.

11. The method according to claim 1, wherein said microfeature forming step further includes the step of forming an additional layer having a higher refractive index than that of the support material to achieve an optical waveguide.

12. The method according to claim 11, including the step of selecting the thickness of said additional layer to provide a desired transparency of said support.

13. The method according to claim 11, including the step of selecting the thickness of said additional layer to provide a desired reflectivity of said support.

14. The method according to claim 1, including the step of forming a dielectric mirror as microfeatures of said support.

15. The method according to claim 1, including the step of forming a diffractive grating as a microfeature of said support, said method further including the step of superimposing said diffractive grating on at least a portion of said grooves.

16. The method according to claim 1, including the step of providing said support with light absorbing pigments.

* * * * *